United States Patent [19]
Reichgott et al.

[11] Patent Number: 5,772,919
[45] Date of Patent: Jun. 30, 1998

[54] METHODS OF INHIBITING CORROSION USING HALO-BENZOTRIAZOLES

[75] Inventors: David W. Reichgott, Seattle, Wash.; Sydia B. Anderson, Doylestown, Pa.; Michael A. Cady, Yardley, Pa.; Roger C. May, Glenside, Pa.; Anita G. Monino, Horsham, Pa.

[73] Assignee: BetzDearborn Inc., Trevose, Pa.

[21] Appl. No.: 778,705

[22] Filed: Jan. 3, 1997

Related U.S. Application Data

[63] Continuation-in-part of Ser. No. 407,173, Mar. 21, 1995, abandoned.

[51] Int. Cl.$^6$ ............................... C09K 3/00; C23F 11/04; C04B 9/02
[52] U.S. Cl. ...................... 252/390; 252/388; 252/390; 252/394; 106/14.16; 106/14.17; 218/698; 422/16
[58] Field of Search ................................ 252/390, 394, 252/388; 106/14.15, 14.16, 14.17; 210/698; 422/16

[56] References Cited

U.S. PATENT DOCUMENTS

| | | | |
|---|---|---|---|
| 3,994,885 | 11/1976 | Koppel | 260/243 |
| 4,044,000 | 8/1977 | Koppel | 260/239 |
| 4,051,320 | 9/1977 | Yanagisawa et al. | 542/420 |
| 4,145,540 | 3/1979 | Ochiai et al. | 544/21 |
| 4,234,678 | 11/1980 | Yoshimoto et al. | 430/564 |
| 4,642,221 | 2/1987 | Hansen et al. | 422/16 |
| 4,744,950 | 5/1988 | Hollander | 422/16 |
| 5,236,626 | 8/1993 | Vanderpool et al. | 252/394 |

FOREIGN PATENT DOCUMENTS 53-018432  2/1978  Japan .

OTHER PUBLICATIONS

Effects of Halogenation on Yellow Metal Corrosion: Inhibition by Triazoles, Corrosion 50, 422 (1994).
Improving the Corrosion Inhibitor Efficiency of Tolytriazole in the Presence of Chloride and Bromine, NACE Corrosion/87, Paper No. 157 (1987).
The Water Drop, vol. 1, No. 2, 1985.
The Performance of Tolyltraizole in the Presence of Sodium Hypochlorite Under Simulated Field Conditions, NACE Corrosion/83, Paper No. 283. (1983).
Effects of Substituted Benzotriazoles on the Electrochemical Behavior of Copper in $h_2SO_4$, Corrosion, vol. 37, No. 4, 223 (1981).
1–Chlorobenzotriazole: a New Oxidant, J. Chem. Soc., pp. 1474–1477 (1969).
The Destruction of Tolytriazole Inhibitor by Chlorination of Cooling Water, Materials Performance pp. 48–52, Aug. 1983.
The Impact of Chlorine on Tolytriazole and Butylbenzotriazole Corrosion Inhibitor Films on copper, Paper IWC–92–40, 1992.
The Chemistry of Azole Copper Corrosion Inhibitors in Cooling Water, NACE–Corrosion, vol. 41, No. 1, pp. 39–45, Jan. 1985.
Surface analytical Investigation of the Impact of Chlorine on Triazole Inhibitor Layers on Copper, NACE Corrosion/93, Paper No. 354 (1993).
Tetrahedron: Asymmetry (1995), vol. 6, No. 12, pp. 2991–3000, as abstracted by Chem Ab. 124:202191.
Zh. Org. Khim (1995), vol. 31, No. 8, pp. 1231–1233, as abstracted by Chem Ab. 124:317068.
JP 04294345 (Jan. 1992) as abstracted by Chem Ab. 119:82791.
JP 54095251 (Jul. 1979) as abstracted by Chem Ab. 92:13673.
J. Chem. Soc. (1978) pp. 909–912, as abstracted by Chem Ab. 89:215304.
DE 2725743 (1977) as abstrated by Chem Ab. 88:97386.

*Primary Examiner*—Richard D. Lovering
*Assistant Examiner*—Deanna Baxam
*Attorney, Agent, or Firm*—Alexander D. Ricci; Steven D. Boyd

[57] ABSTRACT

The use of halo-benzotriazoles as corrosion inhibitors in aqueous systems is disclosed. Halo-benzotriazoles such as chloro-tolyltriazole and bromo-tolyltriazole were found to be more effective corrosion inhibitors than tolyltriazole in the presence of chlorine.

8 Claims, No Drawings

METHODS OF INHIBITING CORROSION USING HALO-BENZOTRIAZOLES

This application is a continuation-in-part of application Ser. No. 08/407,173 filed Mar. 21, 1995, now abandoned.

FIELD OF THE INVENTION

The present invention relates to the control of corrosion in aqueous systems. More particularly, the present invention relates to the inhibition of corrosion of steel and copper alloys in aqueous systems through application of halo-benzotriazoles to the aqueous system.

BACKGROUND OF THE INVENTION

The use of triazoles for inhibiting the corrosion of copper and iron alloys in a wide variety of aqueous and non-aqueous systems is well known. In industrial cooling water systems, benzotriazole and tolyltriazole are used most often. Tolyltriazole is generally preferred because of its lower cost. Triazoles are film forming materials that provide efficient coverage of metal or metal oxide surfaces in a system thereby providing protection against corrosive elements present in an aqueous system. In addition to the film forming tendency of various azoles, they also precipitate soluble, divalent copper ions. The precipitation prevents transport of copper ions to ferrous surfaces, where galvanic reactions between copper ions and iron atoms leads to pitting corrosion of the ferrous metal.

While the use of azoles for corrosion inhibition is widespread, there are drawbacks to their use, specifically with tolyltriazole. The most important drawbacks are experienced when azoles are used in combination with oxidizing halogens. Oxidizing halogens such as elemental chlorine, bromine, their hypohalous acids, or their alkaline solutions (i.e., solutions of hypochlorite or hypobromite ion) are the most common materials used to control microbiological growth in cooling water systems. When copper or iron alloys that have previously been protected with azoles are exposed to an oxidizing halogen, corrosion protection breaks down. After breakdown, it is difficult to form new protective films in tolyltriazole treated cooling systems that are being chlorinated, particularly continuously chlorinated. Very high dosages of tolyltriazole are frequently applied in an attempt to improve performance, often with limited success.

The degradation of protection of azole films in the presence of oxidizing halogens is well-documented in the literature. For example, R. Holm, et al., concluded that hypochlorite penetrates an intact triazole film, leading to higher corrosion rates, and that secondly, hypochlorite attacks the prefilmed triazole surface, disrupting or degrading the film (53rd Annual Meeting of the International Water Conference, Paper No. IWC-92-40, 1992). Lu, et al., also studied interactions of triazole films with hypochlorite on copper and copper alloy surfaces ("Effects of Halogenation on Yellow Metal Corrosion: Inhibition by Triazoles", Corrosion, 50, 422 (1994)). Lu, et al., concluded:

(a) prefilmed tolyltriazole on copper and brass surfaces undergoes decomposition during chlorination;
(b) the stability of prefilmed tolyltriazole on copper and brass to NaOCl was improved when tolyltriazole was added to the hypochlorite solution;
(c) clean (i.e., non-prefilmed) copper surfaces did not develop good protective films when placed in solutions containing mixtures of tolyltriazole and NaOCl.

Thus, the combination of tolyltriazole with NaOCl did not produce a composition capable of efficient film formation and corrosion inhibition.

The nature of the reaction products when azoles are exposed to oxidizing halogens in a cooling water system is not clear. The literature teaches that a compound is formed when chlorine and tolyltriazole are combined in cooling waters, and that it responds to analytical tests for chlorine. For example, Vanderpool, et al., state that chlorine reacts reversibly with tolyltriazole to produce N-chloro-tolyltriazole. They specifically state, "presumably this compound is not itself an inhibitor." Rather, they teach that it is readily hydrolyzed to the original tolyltriazole and hypochlorous acid so that free tolyltriazole becomes available for corrosion inhibition ("Improving the Corrosion Inhibitor Efficiency of Tolyltriazole in the Presence of Chlorine and Bromine", NACE Corrosion/87, Paper No. 157 (1987)). Hollander and May stated they were able to isolate lchloro-tolyltriazole from stored, more highly concentrated solutions, but they also teach that "at low concentrations (less than 10 mg/L) rapid hydrolysis made it impossible to isolate the chloro adducts." Based upon proton NMR analysis, the material Hollander and May isolated was chloro-tolyltriazole.

Another observation is that a very characteristic odor is present whenever tolyltriazole and chlorine are combined in cooling waters.

In contrast, the present authors have shown that chloro-tolyltriazole does not respond to analytical tests for chlorine, despite extended boiling. And solutions of chloro-tolyltriazole, surprisingly, do not produce the characteristic odor. Thus chloro-tolyltriazole is clearly different from the tolyltriazole-chlorine reaction product that forms in -situ in cooling water systems.

There are also references in the literature to 5-chlorobenzotriazole (i.e., CAS number [94-97-3]). In "The Water Drop", Volume I No. 2, 1985, Puckorius & Associates state that chlorinated tolyltriazole is effective as a corrosion inhibitor and cite R. P. Carr as a reference. A literature review of published work by Carr indicates that he actually teaches that reactions between tolyltriazole and chlorine do not occur under cooling water conditions ("The Performance of Tolyltriazole in the Presence of Sodium Hypochlorite Under Simulated Field Conditions", NACE Corrosion/83 Paper No. 283, 1983). In this Corrosion/83 paper, Carr does discuss the inhibiting action of a chloro-azole but it is a reference to earlier literature and specifically to the action of 5-chlorobenzotriazole and related aryl substituted azoles in sulfuric acid solutions ("Effects of Substituted Benzotriazole on the Electrochemical Behavior of Copper in $H_2SO_4$", Wu et al., Corrosion, Volume 37, No. 4, 223 (1981)). Since the 1985 Puckorius reference, there has been widespread use of tolyltriazole in chlorinated cooling systems with well established performance difficulties, indicating a continuing, unsolved problem in the art.

Other problems are well-known when tolyltriazole and oxidizing halogens are combined in cooling waters. These include a loss in the extent of precipitation of transition metal ions such as copper, thus leading to improved transport and galvanic corrosion, a change in the response of the standard spectrophotometric test for tolyltriazole, leading to unintentional overfeed, and the objectionable odor mentioned above. This odor can be sensed even when the cooling water originally contained 1 ppm tolyltriazole, or less. Since cooling water often passes over cooling towers, evaporation and drift release the objectionable odor to the local environment.

The present inventors believe that the odorous material is N-chloro-tolyltriazole, that it forms OCl reversibly with tolyltriazole in dilute solution, and that it is absent in the final product when the reaction is run in concentrated solution, i.e., tolyltriazole+OCl→N-chloro-tolyltriazole-(intermediate)→chloro-tolyltriazole. The present inventors have found no evidence of reversion of chloro-tolyltriazole to either the odorous intermediate or to tolyltriazole. Nor is there any evidence of reactions between hypochlorite and chloro-tolyltriazole in dilute aqueous solutions.

SUMMARY OF THE INVENTION

The present inventors have discovered that halo-benzotriazoles such as chloro-tolyltriazole and bromo-tolyltriazole are more effective than tolyltriazole in inhibiting corrosion in aqueous systems. The halo-benzotriazoles are substantially more effective than tolyltriazole in the presence of chlorine. Furthermore, when chloro-tolyltriazole is exposed to chlorine, an objectionable odor does not form and the quantity of chlorine that is required to produce a residual in the aqueous system is reduced.

DESCRIPTION OF THE PREFERRED EMBODIMENTS

The present inventors have discovered that halo-benzotriazoles such as chloro-tolyltriazole and bromo-tolyltriazole are more effective than tolyltriazole in inhibiting corrosion in aqueous systems. The halo-benzotriazoles are substantially more effective corrosion inhibitors than tolyltriazole in the presence of chlorine. The efficacy of the present invention is surprising given the prior knowledge that chlorination of an azole treated system leads to degradation of corrosion inhibition performance. Furthermore, the halo-benzotriazoles of the present invention are not subject to the formation of objectionable odors when exposed to chlorine as is tolyltriazole, the quantity of chlorine that is required to produce a residual in the aqueous system is notably reduced in comparison to systems treated with tolyltriazole, and the treatment is effective in the presence of sulfide ions.

It was discovered that the ex situ preparation of a halo-benzotriazole provided a corrosion inhibitor which exhibited a surprising and unexpected activity when compared to a treatment comprising a mixture of a benzotriazole and a halogen. The results of the studies of the present invention clearly show that mere mixtures of a benzotriazole and a halogen in a cooling water system do not provide the corrosion inhibiting effect of the addition of a halo-benzotriazole prepared ex situ. As further evidence of the surprising activity of an ex situ prepared halo-benzotriazole, the present inventors found that the chlorine demand of a system treated in accordance with the present invention was significantly reduced. Furthermore, in systems treated in accordance with the present invention the objectionable odor common to systems treated with a triazole and halogen was absent.

The halo-benzotriazoles of the present invention can include chloro-, fluoro-, bromo- and iodo- as well as haloalkyl (trifluoromethyl) benzotriazoles. Preferred are chloro-tolyltriazole and bromo-tolyltriazole. The azole may include tolyltriazole, benzotriazole, butylbenzotriazole, mercaptobenzothiazole and the like. The preferred azole is tolyltriazole.

The preferred benzotriazole, tolyltriazole, is such that the preferred halo-benzotriazole is chloro-tolyltriazole or bromo-tolyltriazole. The preparation of the preferred chloro-tolyltriazole can be by any suitable means. Examples of preparation methods include but are not limited to reactions with hypochlorite, N-chlorosuccinimide, and other chlorinating agents. A method of forming chloro-tolyltriazole is through the reaction of tolyltriazole with hypochlorite, in which case the final reaction mixture is an alkaline solution that can be used with or without further modification. Alternatively, chloro-tolyltriazole can be formed through the reaction of tolyltriazole with hypochlorite in acetic acid solutions, (i.e., hypochlorous acid) and then isolated as a solid. For convenience of application, the solid can be redissolved in alcohols such as methanol or 2-propanol, aqueous solutions of alcohols or strong alkaline solutions such as sodium hydroxide or potassium hydroxide.

The preparation of bromo-tolyltriazole can be by any suitable means. Examples of preparation methods include but are not limited to reactions with hypobromite, bromine, and other brominating agents. A method of forming bromo-tolyltriazole is through the reaction of tolyltriazole with bromine in an aqueous solution and then isolating it as a solid. For convenience of application, the solid can be dissolved in a strong alkaline solution such as sodium hydroxide or potassium hydroxide.

In treating an aqueous system in accordance with the present invention, the chloro-tolyltriazole (hereinafter Cl-TTA) is preferably fed continuously to the water. A preferred treatment concentration ranges from about 0.5 to 10 parts per million, most preferably at about 3 parts per million. Continuous feed is not, however, a requirement. The chloro-tolyltriazole can be fed at a concentration sufficient to form a protective film and thereafter feed can be discontinued for extended periods of time.

The halo-benzotriazole treatment of the present invention can be used in combination with other corrosion and/or deposit inhibiting treatments known in the art including but not limited to phosphates, phosphonates, acrylic homo- and copolymers, chelants, and oximes.

The present invention will now be further described with reference to a number of specific examples which are to be regarded solely as illustrative and not as restricting the scope of the present invention.

EXAMPLES

Example 1

The preparation of the solid samples was as follows:

Tolyltriazole (hereinafter TTA) (30 g, 0.225 mol) was dissolved in aqueous acetic acid (60 mL, 1:1 ratio) by heating to 32° C. Sodium hypochlorite (366 g, 5.25% sodium hypochlorite as a bleach solution) was added while maintaining the reaction temperature at ~20° C. Following the addition, the reaction mixture was stirred at room temperature for 24 hours. A sticky precipitate formed during this time. The solid was filtered and taken into methylene chloride. The solid that did not dissolve was filtered and identified as a mixture of Cl-TTA with minor amounts of TTA and dichloro-tolyltriazole (di-Cl-TTA). The methylene chloride was removed to obtain a yellow solid which was identified as a mixture of Cl-TTA with minor amounts of di-Cl-TTA. Unless noted, this latter solid was used in the following Examples.

Example 2

A slurry of TTA (50 g, 0.376 mol) in 25 g of water was warmed to 35° C. Sodium hypochlorite (27.9 g, 0.376 mol, added as 226.8 g of a 12.3% sodium hypochlorite solution) was added over a period of 2 hours. After the addition, the reaction was kept at 45° C. for one hour. During the addition the pH of the reaction mixture increased to 12 and the solids dissolved. The final product was analyzed by $^1$H and $^{13}$C NMR and LC-UV and found to be composed of 81.9% Cl-TTA, 8.8% residual TTA, and 9.3% di-Cl-TTA based on the relative areas in the UV spectra.

On dilution to 1 to 100 ppm azole, with or without pH adjustment to about 7.2, there was no odor from the halobenzotriazole solution of the present invention.

Example 3

In the schemes below, TTA was present at 100 ppm, in contrast to Example 2 where the initial slurry contained about 200,000 ppm. "x" denotes a stoichiometric ratio.

Scheme 1

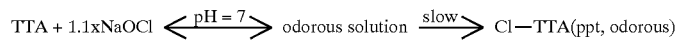

Scheme 2

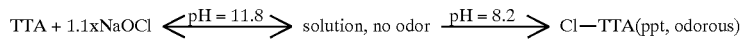

Example 4

Cl-TTA, prepared as a solid according to Example 1, was dissolved in methanol and charged to a simulated cooling water solution. The solution contained 319 ppm Ca (calculated as $CaCO_3$), 7 ppm Mg (calculated as $CaCO_3$), 190 ppm $NaHCO_3$, 882 ppm $Na_2SO_4$, 1184 ppm NaCl, 5 ppm Cl-TTA, and 2.4 ppm of hydroxyethylidene diphosphonic acid (HEDP). Hypochlorite was absent. The solution was maintained at 120° F. by an admiralty brass heater tube and at pH=7.2 to 7.5 by a pH controller equipped to feed sulfuric acid on demand. The solution was recirculated past the heater and past both admiralty and copper/nickel alloy corrosion rate meters (CRM). After 1 hour the solution was drained and replaced by an identical solution with no Cl-TTA. This solution was fed to overflow which replenished the system with fresh solution at a rate of about 4% by volume per hour. This system was maintained under these conditions continuously until the bright admiralty tube was tarnished, at which point the experiment was terminated. Comparisons were made to identical experiments with TTA and benzotriazole.

TABLE I

| | Admiralty Tube Appearance | | |
|---|---|---|---|
| Pretreatment | 40 hours | 94 hours | 336 hours |
| Cl-TTA | Bright | Bright | Tarnished |
| TTA | Bright | Tarnished | * |
| Benzotriazole | Tarnished | * | * |

TABLE II

| | Admiralty Corrosion Rate (mpy) | | | Cu/Ni Corrosion Rate (mpy) | | |
|---|---|---|---|---|---|---|
| Pretreatment | 40 hrs. | 94 hrs. | 336 hrs. | 40 hrs. | 94 hrs. | 336 hrs. |
| Cl-TTA | 0.2 | 0.3 | 0.5 | 0.7 | 0.4 | 0.8 |
| TTA | <0.1 | 2.2 | * | N/A | 5.2 | * |
| Benzotriazole | 1.3 | * | * | 2.0 | * | * |

*Experiment previously terminated.

Example 5

Corrosion tests were carried out in the apparatus described in Example 4 with water containing 500 ppm Ca, 250 ppm Mg, 25 ppm M-alkalinity as $CaCO_3$, 15 ppm o-$PO_4$, 3 ppm tetrapotassium pyrophosphate, 10 ppm of a 3:1, low molecular weight, acrylic acid/allyl 2-hydroxypropyl sulfonate ether copolymer, 2.4 ppm HEDP, a 3 ppm of either Cl-TTA or TTA. The pH was maintained at 7.2 with a blended mixture of air and carbon dioxide at 120° F. for 18 hours. Electrochemical corrosion rates were measured using admiralty brass (ADM) and low carbon steel (LCS) working electrodes. All tests also had both admiralty and LCS coupons in contact with the solution. The method differed from Example 4 in that the azole was fed continuously at 3 ppm during these experiments. The azole was supplied by dissolving the solid in potassium hydroxide solution and then diluting it into the feedwater for the system. Each experiment was duplicated: once with an admiralty brass heated tube, and once with a low carbon steel heated tube. Corrosion rates were measured as in Example 4 from admiralty and LCS working electrodes, and by weight changes of admiralty and LCS coupons. Rates for the coupons were measured for the initial day of each run, and a "differential" rate was calculated for the remaining days of the run by offsetting the initial rate from the overall rate.

TABLE III

| CRM Corrosion Rates: Values at end of six days (mpy) | | | | |
|---|---|---|---|---|
| | LCS Heated Surface | | ADM Heated Surface | |
| | Cl-TTA | TTA | Cl-TTA | TTA |
| LCS | 0.2 | 0.4 | 0.45 | 0.75 |
| ADM | 0.00 | 0.00 | 0.05 | 0.07 |

TABLE IV

| Gravimetric Coupon Corrosion Rates (mpy) (First day and differential rates) | | | | |
|---|---|---|---|---|
| | LCS Heated Surface | | ADM Heated Surface | |
| | Cl-TTA | TTA | Cl-TTA | TTA |
| Day 1 LCS | 4.6 | 3.0 | 3.4 | 2.9 |
| Day 6 LCS (diff.) | 0.25 | 0.33 | 0.25 | 0.25 |
| Day 1 ADM | 1.9 | 2.1 | 1.6 | 1.8 |
| Day 6 ADM (diff.) | 0.00 | 0.20 | 0.00 | 0.10 |

Example 6

The method of Example 5 was followed, except a solution of sodium hypochlorite was added after 20 hours and continued for an additional 72 hours. The feed rate of the sodium hypochlorite was controlled to produce a "chlorine residual" of about 0.1 to 0.3 ppm as $Cl_2$ using a standard DPD spectrophotometric test on the recirculating water. For the experiment with Cl-TTA, the feed rate of the sodium hypochlorite was about 30% of that required for TTA. For TTA, the characteristic odor was detected immediately after the first hypochlorite was added. With Cl-TTA, there was no odor upon initiating hypochlorite addition, and only a trace was sensed just prior to concluding the four day run.

TABLE V

CRM Corrosion Rates: Values at 90 hour mark (mpy)

| | LCS Heated Surface | |
|---|---|---|
| | Cl-TTA | TTA |
| LCS | 0.5 | 2.3 |
| ADM | 0.06 | 0.02 |

TABLE VI

Gravimetric Corrosion Rates (mpy)

| | LCS Heated Surface | |
|---|---|---|
| | Cl-TTA | TTA |
| Day 2 to 4 LCS | 1.1 | 2.6 |
| Day 4 LCS (diff.) | 0.4 | 1.4 |
| Day 2 to 4 ADM | 1.1 | 1.2 |
| Day 4 ADM (diff.) | 0.15 | 0.85 |

Example 7

Solutions of azole at 6 ppm were made in deionized water, and the pH was adjusted to 7.0. $Cu^{+2}$ ion was added (0.1 ppm from cupric sulfate) and the pH was again adjusted to 7.0. A sample was digested with nitric acid, analyzed for copper, and a second sample was filtered (0.2 micron pore size), digested, and analyzed for copper. The ratio was expressed as "% soluble Cu":

TABLE VII

| Sample | % Soluble Cu |
|---|---|
| TTA | 15 |
| TTA + NaOCl | 90 |
| Cl-TTA | 13 |

Example 8

Admiralty brass corrosion coupons and working electrodes were coated with a sulfide layer by exposing the metal to a sodium sulfide solution for 18 hours. These samples were rinsed and dried. Corrosion tests were carried out in aqueous solutions in stirred beakers containing 500 ppm Ca, 250 ppm Mg, 25 ppm Malk, 15 ppm o-$PO_4$, 3 ppm tetrapotassium pyrophosphate, 10 ppm of a 3:1, low molecular weight, acrylic acid/allyl 2-hydroxypropyl sulfonate ether copolymer, 2.4 ppm HEDP, and the pH was maintained at 7.2 with a blended mixture of air and carbon dioxide at 120° F. for 18 hours. Electrochemical corrosion rates were measured using admiralty brass or low carbon steel working electrodes. All tests also had both admiralty and LCS coupons in contact with the solution.

Each solution was tested with and without addition of sodium hypochlorite (added after 1 hour exposure). In a separate, but otherwise identical experiment, clean low carbon steel working electrodes were used in place of the sulfide-exposed admiralty brass, but the sulfide-exposed brass coupons were present as a source of copper. At the conclusion of the experiment, a sample of the supernatant solution was taken and analyzed for copper. Analyses were taken with and without filtration through a 0.2 micron membrane filter.

TABLE VIII

| Azole | NaOCl (ppm) | Admiralty Brass Corrosion Rate (mpy) | Low Carbon Steel Corrosion Rate (mpy) | Copper (ppm) | |
|---|---|---|---|---|---|
| | | | | Unfiltered | Filtered |
| none | 0 | 1.01 | 5.4 | 0.354 | 0.103 |
| 3 ppm TTA | 0 | 0.07 | 1.2 | 0.014 | 0.014 |
| 3 ppm Cl—TTA | 0 | 0.06,0.05 | 1.0 | 0.005 | 0.004 |
| none | 2.0 | 2.09 | 5.2 | 0.417 | 0.059 |
| 3 ppm TTA | 2.0 | 0.45 | 2.6 | 0.133 | 0.066 |
| 3 ppm Cl—TTA | 2.0 | 0.13 | 1.7 | 0.086 | 0.039 |

Example 9

A synthetic sea water was formulated from deionized water plus 1010 ppm Ca as $CaCO_3$, 5226 ppm Mg (as $CaCO_3$), 18971 ppm Cl, 2660 ppm $SO_4$, 117 ppm M-alkalinity (as $CaCO_3$), 5 ppm azole (see below), and the pH was maintained at 7.8 with a blended mixture of air and carbon dioxide at 100° F.

Admiralty brass electrodes were exposed to this medium for 1 hour and then they were transferred to identical water with no azole present. Electrochemical corrosion rates were measured for 18 hours.

TABLE IX

| Azole | Mean Electrochemical Corrosion Rate (mpy) |
|---|---|
| Benzotriazole | 40 |
| 5-Butylbenzotriazole | 15 |
| Tolyltriazole | 6 |
| Chloro-tolyltriazole | 3.2 |

Example 10

Sodium hypochlorite (12.2%, 204.9 g, 0.336 mol) was added over 90 minutes to a stirring slurry of benzotriazole (40 g, 0.336 mol) in 30 g of water at room temperature. Following the addition, the reaction mixture was held at 45°–50° C. for one hour. Upon cooling, a precipitate formed. A clear yellow solution was obtained after adjusting the pH to 11. The final product was analyzed by LC/MS and $^{13}C$ and $^1H$ NMR and found to be composed of 54.6% chloro-benzotriazole (Cl-BZT), 23.9% residual benzotriazole, and 21.5% di-chloro-benzotriazole (di-Cl-BZT).

Example 11

Bromine (12.5 g, 0.078 mol) was added to a stirring slurry of TTA (10 g, 0.075 mol) in 66 g of water in a reactor protected from light, while maintaining the temperature at <25° C. After the addition, the reaction mixture was held at 35°–40° C. for one hour. Upon cooling, adjusting the pH to 11–12 did not produce a clear solution. The small amount of precipitate that formed upon standing was removed by filtration, the pH of the filtrate was adjusted to neutral, and the resulting precipitate filtered. This solid was characterized by LC/MS and $^{13}$C and $^1$H NMR and found to be composed of 90.5% bromo-tolyltriazole (Br-TTA), 4.9% residual TTA, and 4.2% di-bromo-TTA.

Example 12

The method of Example 8 was followed, using samples from Examples 2, 11 and 12 at 1 to 4 ppm total actives. The following were the 18 hour averaged electrochemical corrosion rates:

TABLE X

| Azole | Conc. (ppm) | Source | NaOCl | Average Corrosion Rate (mpy) |
|---|---|---|---|---|
| Cl—BZT | 1 | Ex. 11 | none | 0.21 |
| | 2 | | | 0.09 |
| | 4 | | | 0.03 |
| Cl—BZT | 1 | Ex. 11 | 2 ppm | 0.55 |
| | 2 | | | 0.25 |
| | 4 | | | 0.09 |
| Cl—TTA | 1 | Ex. 2 | none | 0.14 |
| | 2 | | | 0.09 |
| | 4 | | | 0.08 |
| Cl—TTA | 1 | Ex. 2 | 2 ppm | 0.58 |
| | 2 | | | 0.24 |
| | 4 | | | 0.09 |
| Br—TTA | 1 | Ex. 12 | none | 0.17 |
| | 2 | | | 0.11 |
| | 4 | | | 0.07 |
| Br—TTA | 1 | Ex. 12 | 2 ppm | 0.45 |
| | 2 | | | 0.16 |
| | 4 | | | 0.09 |
| TTA | 1 | | none | 0.13 |
| | 2 | | | 0.14 |
| | 4 | | | (n/a) |
| TTA | 1 | | 2 ppm | (n/a) |
| | 2 | | | 0.45 |
| | 4 | | | 0.27 |

The above examples show that the halo-benzotriazoles of the present invention are effective corrosion inhibitors even in the presence of chlorine.

While the present invention has been described with respect to particular embodiments thereof, it is apparent that numerous other forms and modifications of this invention will be obvious to those skilled in the art. The appended claims and this invention generally should be construed to cover all such obvious forms and modifications which are within the true spirit and scope of the present invention.

What is claimed is:

1. A method of inhibiting corrosion of metal surfaces contacted by an aqueous system being treated with a halogen comprising adding to said aqueous system being treated with a halogen an amount effective for the purpose of inhibiting corrosion of a halo-benzotriazole prepared ex-situ said aqueous system.

2. The method of claim 1 wherein sulfide ions are present in said aqueous system.

3. The method of claim 1 wherein said halo-benzotriazole is selected from the group consisting of chloro-tolyltriazole and bromo-tolyltriazole.

4. The method of claim 1 wherein said halo-benzotriazole is added to said aqueous system at a concentration of greater than about 0.5 parts per million.

5. The method of claim 1 wherein said halo-benzotriazole is added to said aqueous system at a concentration of from about 0.5 parts per million to about 10 parts per million.

6. A method of forming a corrosion inhibiting layer on a metal surface in contact with an aqueous system being treated with a halogen comprising adding to said aqueous system an amount effective for the purpose of inhibiting corrosion of a halo-benzotriazole prepared ex-situ said aqueous system.

7. A method of inhibiting copper ion transport in an aqueous system being treated with a halogen in contact with metal surfaces including copper comprising adding to said aqueous system an amount effective for the purpose of inhibiting corrosion of a halo-benzotriazole prepared ex-situ said aqueous system.

8. A method of inhibiting corrosion of metal surfaces contacted by an aqueous system being treated with a halogen comprising adding to said aqueous system an amount effective for the purpose of inhibiting corrosion of a halo-benzotriazole formed by the ex situ reaction of tolyltriazole and hypochlorite.

* * * * *